United States Patent [19]

Rosenblatt et al.

[11] Patent Number: 5,001,223
[45] Date of Patent: Mar. 19, 1991

[54] PARATHYROID HORMONE ANTAGONISTS WITH ENHANCED METABOLIC PROPERTIES

[75] Inventors: Michael Rosenblatt, Ardmore; Lynn H. Caporale, Lansdale, both of Pa.; Michael Chorev, Jerusalem, Israel

[73] Assignee: Merck & Co., Inc., Rahway, N.J.

[21] Appl. No.: 318,475

[22] Filed: Mar. 2, 1989

Related U.S. Application Data

[63] Continuation of Ser. No. 54,360, May 26, 1987, abandoned.

[51] Int. Cl.[5] ............................................. C07K 7/10
[52] U.S. Cl. .................................... 530/324; 530/325
[58] Field of Search ............... 530/324, 350, 399, 375; 514/12

[56] References Cited

U.S. PATENT DOCUMENTS

| | | | |
|---|---|---|---|
| 4,423,037 | 12/1983 | Rosenblatt et al. | 530/324 |
| 4,656,250 | 4/1987 | Morita et al. | 530/324 |

FOREIGN PATENT DOCUMENTS

| | | | |
|---|---|---|---|
| 0177819 | 4/1986 | European Pat. Off. | 514/12 |
| 0113753 | 9/1980 | Japan | 514/12 |
| 0096052 | 6/1983 | Japan | 530/324 |
| 0042351 | 3/1984 | Japan | 530/324 |
| 0204159 | 11/1984 | Japan | 530/324 |
| 86/03496 | 6/1986 | PCT Int'l Appl. | 514/12 |

OTHER PUBLICATIONS

Biochemistry, 1981, vol. 20, 1981, 7246-7250; "Sulfur-Free PTH Analogues Containing D-Amino Acids; Biological Properties in Vitro or in Vivo".

*Primary Examiner*—Ronald W. Griffin
*Assistant Examiner*—T. D. Kiessendorf
*Attorney, Agent, or Firm*—Charles M. Caruso; Mark R. Daniel

[57] ABSTRACT

The present invention relates to the use of peptide hormone analogues as inhibitors of their respective naturally occurring peptide hormone. The structure of the peptide hormone analogues is exemplified by parathyroid hormone wherein Phe[7] is substituted by NMePhe, D-Phe, desamino Phe, or Met[8] is substituted by NMe-Met.

2 Claims, No Drawings

PARATHYROID HORMONE ANTAGONISTS WITH ENHANCED METABOLIC PROPERTIES

This is a continuation of application Ser. No. 054,360, filed May 26, 1987, now abandoned.

BACKGROUND OF THE INVENTION

This invention relates to the use of peptide hormone analogues for inhibiting the naturally occurring hormone peptide in vivo and in vitro. These peptide hormone analogues when administered to a vertebrate, such as mammals, block the endrocrine activity of the peptide hormone or other analogous molecules. These peptide hormone analogues are also useful in vitro in combination with a bioassay for the naturally occurring hormone. The peptide hormone analogues are useful in treating various diseases caused by hormone excess and in treating hormone dependent tumors. One example of this invention relates to the synthesis of parathyroid hormone analogues useful for inhibiting the action of parathyroid hormone both in vivo and in vitro.

Analysis of the relation of structure to hormonal function has provided important insights into the mechanism of action of peptide hormones. Each type of peptide hormone has an affinity for specific receptors to which it binds. Upon binding, the peptide hormone acts either directly or causes a change in the intracellular concentration of a second messenger molecule such as cyclic AMP, cyclic GMP, or calcium ions. These second messenger molecules, in turn, cause changes in the metabolism or physiology of the cell. These changes in cell metabolism or physiology are directly or indirectly dependent upon the binding of the peptide hormone to its specific cell surface receptor. Therefore, if the cell surface receptor is blocked then the hormone effect is also blocked.

Peptide hormone analogues have long been known as a method through which the biochemistry of hormones can be studied and evaluated. Endocrinologists have long desired a method for producing a class of peptide hormone analogues which would allow the blocking of specific hormone receptors without activating a change in the second messenger molecules, thereby avoiding the hormone induced metabolic changes.

Rosenblatt et al., U.S. Pat. No. 4,423,037 and the publications referred to therein describe the structure of certain peptide hormone analogues and their binding to cell receptors. In particular, these publications describe the properties of parathyroid hormone analogues and their physiological properties.

Scientific efforts over a period of many years have sought to understand the interaction between peptide hormones and the cell surface receptor specific for each peptide hormone. One of the peptide hormones, parathyroid hormone, has been studied by using analogues of parathyroid hormone (PTH). One objective of these studies has been to understand the binding of the peptide hormone to the cell surface receptor such that an analogue could be constructed which would bind with the same or greater affinity than the naturally occurring hormone. This analogue would enable the peptide hormone analogue of parathyroid hormone to be used to block the effect of the naturally occurring parathyroid hormone. One of the major problems encountered in this search for a clinically and pharmacologically effective parathyroid hormone analogue was the problem of agonist activity. Agonist activity is the property of the peptide hormone analogue to itself stimulate the change in second messengers which brings about the physiological change associated with the naturally occurring hormone. Therefore, the problem was to create hormone analogues which would bind with high affinity to the appropriate hormone cell surface receptor but not stimulate a change in the second messenger concentration, that is, not act as hormone itself. These analogues could then be used in treating hormone related diseases.

It is a primary object of the present invention to provide PTH analogues with increased metabolic half-life by stabilizing them against enzymatic degradation, particularly degradation by amino peptidases. Thus, these PTH analogues have increased in vivo potency.

Another object of the present invention is to provide novel PTH analogues. Another object of the present invention is to provide a method of inhibiting the action of PTH through the administration of novel PTH analogues. Still another object of the invention is to provide PTH analogues wherein amino acid modifications result in binding to all the surface receptor without activating the second messenger molecule. The above and other objects are accomplished by the present invention in the manner more fully described below.

SUMMARY OF THE INVENTION

The present invention provides a peptide which comprises [Tyr$^{34}$]PTH(7-34)NH$_2$ wherein Phe$^7$ is substituted by NMePhe, D-Phe, desamino Phe, or Met$^8$ is substituted by NMeMet. The invention also provides peptides comprising [Nle$^{8,18}$,Tyr$^{34}$]PTH(7-34)NH$_2$ wherein Phe$^7$ is substituted by NMePhe, D-Phe or desamino Phe. The PTH can be human parathyroid hormone (hPTH), bovine parathyroid hormone (bPTH) or rat parathyroid hormone (rPTH).

The particular PTH analogues have one of the following structures: [NMePhe$^7$Tyr$^{34}$]h PTH(7-34)NH$_2$; [NMePhe$^7$Tyr$^{34}$]b PTH(7-34)NH$_2$; [desamino Phe$^7$]h PTH(7-34)NH$_2$; [desamino Phe$^7$]b PTH(7-34)NH$_2$; [D-Phe$^7$,Tyr$^{34}$]h PTH(7-34)NH$_2$; [D-Phe$^7$,Tyr$^{34}$]bPTH(7-34)NH$_2$; [NMeMet$^8$Tyr$^{34}$]h PTH(7-34)NH$_2$; [NMeMet$^8$Tyr$^{34}$]b PTH(7-34)NH$_2$.

The present invention also provides a method of inhibiting the action of parathyroid hormone comprising the administration of therapeutically effective amount of a parathyroid hormone analogue described above. The present invention also provides a method of treating osteoporosis or hypercalcemia comprising the administration of a therapeutically effective amount of a parathyroid hormone analogue described above. A method of treating hyperparathyroidism comprising the administration of a therapeutically effective amount of the parathyroid hormone analogues of this invention is also provided. A method of treating hyperparathyroidism expressed as a hypercalcemic crisis, renal failure or hypertension is also provided. A method of treating the disease state produced by a tumor or other cell overproducing a peptide hormone-like molecule and method of treating immune diseases wherein the disease state comprises inflammation, an allergic response, or hyperactive lymphocytes is also provided by the novel peptide hormone analogues of the present invention.

DETAILED DESCRIPTION OF THE INVENTION

Various other objects, features and attendant advantages of the present invention will be more fully appreciated as the same becomes better understood from the following detailed description.

Extensive structure and activity studies have now led to the design of peptide hormone analogues which have high binding affinity for their respective cell surface receptors while not stimulating the production of second messenger molecules. An example of such a peptide hormone analogue is [desamino Tyr$^{34}$]bPTH(7-34)NH$_2$[NMePhe$^7$,Tyr$^{34}$]bPTH(7-34)NH$_2$ which inhibits PTH in vivo but does not act as an agonist.

Agonist activity is dependent upon the presence of the N-terminal amino acid sequence. The removal of the two to six end terminal amino acids results in the loss of most if not all agonist activities. Therefore, the second messenger molecules are not affected by those analogues which have the altered amino terminus.

PTH analogues with two to six amino acids removed from the N-terminus produces an inhibitor which still binds with high affinity to the peptide hormone receptor without causing a change in cyclic AMP concentration.

The following is the 34-amino acid sequence of bovine parathyroid hormone (bPTH):

H2N—ALA—VAL—SER—GLU—ILE—GLN—PHE—MET—HIS—ASN—LEU—GLY—

LYS—HIS—LEU(15)—SER—SER—MET—GLU—ARG—VAL—GLU—TRP—LEU—

ARG—LYS—LYS—LEU—GLN—ASP(30)—VAL—HIS—ASN—PHE—COOH.

The following is the 34-amino acid sequence of human parathyroid hormone (hPTH):

H2N—SER—VAL—SER—GLU—ILE—GLN—LEU—MET—HIS—ASN(10)—LEU—

GLY—LYS—HIS—LEU—ASN—SER—MET—GLU—ARG(20)—VAL—GLU—TRP—

LEU—ARG—LYS—LYS—LEU—GLN—ASP(30)—VAL—HIS—ASN—PHE—COOH.

The following is the 34-amino acid sequence of rat parathyroid hormone (rPTH):

H2N—ALA—VAL—SER—GLU—ILE—GLN—LEU—MET—HIS—ASN(10)—

LEU—GLY—LYS—HIS—LEU—ALA—SER—VAL—GLU—ARG(20)—

MET—GLN—TRP—LEU—ARG—LYS—LYS—LEU—GLN—ASP(30)—

VAL—HIS—ASN—PHE—COOH.

Fragments of peptide hormones containing the region specific for binding to the cell surface receptor can be used as inhibitors or blocking agents. For parathyroid hormone, the N-terminal 34 amino acids are sufficient to define binding specificity to the parathyroid hormone cell surface receptor. This receptor specificity is further defined by the following publication herein incorporated by reference: M. Rosenblatt, et al., Endocrinology, 107:2, 545–550, 1980 and S. R. Nussbaum, et al., Journal of Biological Chemistry, 255:10183, 1980.

The presence of D-amino acids in peptide hormone in place of L-amino acids results in a peptide resistant to catabolism. However, not all such substitutions result in an active peptide hormone. The insertion of D-tyrosine at position 34 in PTH results in a significant increase in the biological activity of the hormone in addition to increasing stability of the peptide. The utilization of D-amino acids in peptide hormone synthesis is described in the following publications herein incorporated by reference: Coltrera, et al., Biochemistry, 19:4380–4385, 1980; Rosenblatt et al., Biochemistry, 20:7246–7250, 1981.

The balance of the description will be divided into two sections. Section I will describe the preparation and structure of inhibitors of peptide hormones, Section II will discuss the use of the peptide hormone inhibitors.

I. Preparation and Structure of Peptide Hormone Inhibitors

The technique of solid-phase peptide synthesis, developed by Merrifield ("Solid-Phase Peptide Synthesis", Advances in Enzymology, 32:221–296, 1969) has been successfully employed in the synthesis of peptide hormones including parathyroid hormone. This method is based on the strategy of having the carboxyl terminus of the peptide linked covalently to a solid support. The desired peptide sequence is prepared by stepwise coupling of single amino acids to a peptide chain growing from the carboxyl toward the amino terminus. Because each amino acid is coupled by nearly the same series of reactions, the need for elaborate strategies in the synthesis is minimized. Solubility is not a major issue during synthesis, because the peptide is linked to a solid support. This method is rapid and it can be utilized by a single worker. It is very convenient for the synthesis of multiple analogues with amino-terminal substitutions, because a single synthesis can be branched in multiple directions near the amino terminus, thereby creating many analogues varying only in the amino terminal region.

II. Use of Peptide Hormone Inhibitors

The method of inhibiting the action of peptide hormones comprises the administration of a therapeutically effective amount of any peptide hormone or analogue wherein the two N-terminal amino acids are removed and zero or more of the next four N-terminal amino acids are removed sequentially from the N-terminus. These hormone analogues retain specificity for the cell surface receptor without stimulating a physiological response. This method of use applies to the entire peptide hormone or its analogue, or to a fragment of the peptide hormone containing the receptor binding site.

The use of peptide hormone analogues is exemplified by parathyroid hormone analogues. The parathyroid hormone may be of bovine, human, rat, or any vertebrate origin. The analogue may contain all the amino acids except for the modified N-terminal region or it might comprise the N-terminal 7-34 amino acids. Individual amino acids can be substituted to improve stability as exemplified by tyrosine or norleucine in the present invention.

The peptide hormone analogues of this invention can be used in vitro to measure the concentration of naturally occurring peptide hormone. This bioassay procedure is illustrated by a bioassay for parathyroid hormone. The unknown concentration of parathyroid hormone in a solution can be determined by measuring the amount of parathyroid hormone analogue required to inhibit its binding to the parathyroid hormone cell surface receptor. The concentration of PTH analogue required to block the action of parathyroid hormone is a direct indicator of the parathyroid hormone concentration.

Parathyroid hormone analogues can be used to diagnose the etiology of or to treat osteoporosis or hypercalcemia through the administration of a therapeutically effective amount of the parathyroid hormone analogues of this invention. Similarly, hyperparathyroidism and other aspects of hyperparathyroidism, such as a hypercalcemic crisis, renal failure or hypertension can be treated through the administration of the parathyroid hormone analogues of this invention.

Tumors and other aberrant cell growth often produce hormone like substances causing a disease state. The use of peptide hormone analogues to block stimulation caused by such hormone like substances can result in the alleviation of the disease state. Therefore, the peptide hormone analogues of the present invention can be administered to treat diseases caused by aberrant production of hormone like substances.

Immune diseases such as inflammation, allergic responses and hyperactive lympocytes can be treated through the administration of peptide hormone analogues which block the action of peptide hormones, such as PTH analogues inhibiting the binding of PTH to cells of the immune system.

The peptide hormone analogues of this invention exhibit both oral and parenteral activity and can be formulated in dosage forms for oral parenteral, rectal, intra-nasal, or topical administration. Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluent. In the case of capsules, tablets, and pills, the dosage forms may also comprise buffering agents. Tablets and pills can additionally be prepared with an enteric coating.

Liquid dosage forms for oral administration include pharmaceutically acceptable emulsion, solutions, suspensions, syrups and elixers containing inert diluents commonly used in the pharmaceutical art. Besides inert diluents, such compositions can also include adjuvants, such as wetting agents, emulsifying and suspending agents, and sweetening. Preparations according to this invention for parenteral administration include sterile aqueous or non-aqueous solutions, suspensions or emulsions. Examples of non-aqueous solvents or vehicles are propylene glycol, polyethylene glycol, vegetable oils such as olive oil and injectable organic esters such as ethyloleate.

Compositions for rectal administration are suppositories which may contain in addition to the active substance, excipients such as cocoa butter or a suppository wax. The dosage of active ingredient in the compositions of this invention may be varied; however it is necessary the amount of the active ingredient shall be such that a suitable dosage form is obtained. The selected dosage form depends upon the desired therapeutic effect, on the route on the administration, and on the duration of the treatment.

Obviously, numerous modifications and variations of the present invention are possible in light of the above teachings. It is therefore to be understood that within the scope of the appended claims, the invention may be practiced otherwise than as specifically described herein.

EXAMPLE 1

Synthesis and Purification of Peptide Hormone Analogues of PTH

Analogues of parathyroid hormone, were prepared by a modification of the solid-phase method of Merrifield. Syntheses were performed using an Applied Biosystems 430A Synthesizer. 4-Methylbenzhydrylamine hydrochloride resin (polystyrene-1% by divinylbenzene, USB) was employed as the solid support in order to effect the carboxyamide ($CONH_2$) COOH-terminal modification.

The tertiary butyloxycarbonyl (Boc) group was used to protect the alpha-amino group of each amino acid during coupling. Side-function protection was afforded as follows: (a) the hydroxyl group of serine was protected as the O-benzyl ether; (b) the hydroxyl group of tryosine as the 0-2,6-dichlorobenzyl ether or p-bromobenzyloxycarbonyl ester; (c) the carboxyl group of glutamic and aspartic acid as the benzyl or cyclohexyl ester; and (d) the imidazole nitrogen of histidine by the benzyloxymethyl (BOM) and the guanidine function of arginine was protected by the p-toluenesulfonyl group, and the indole amine by formyl groups. All amino acids were obtained from Applied Biosystems, Inc., Peninsula Laboratories, or Bachem Chemicals.

The peptide-resin synthesis were carried out using Applied Biosystems, Inc. specified protocols. Double couplings were carried out for the incorporation of each amino acid. Deprotection times with trifluoroacetic acid were extended 6 minutes over manufacturer protocols.

The peptide was cleaved from the copolymer resin with simultaneous removal of the side-chain protecting groups similar to the 2 step HF cleavage procedure described by Tam J.A.C.S. 105: 6442-6455 (1983).

In the first HF step the following ratios of reagents were used: 5% p-cresol, 5% p-thiocresol, 65% dimethyl sulfide and 25% HF. 10 ml of mixture per gram of peptide-resin was used for 2 hours at 0° C. In the second HF step the following ratio of reagents were used: 5% p-cresol, 5% p-thiocresol and 90% HF. The cleavage was carried out for 75 min. at 0° C. After removal of HF the peptide-resin mixture was washed with anhydrous ether to remove scavenger. The peptide was then extracted with 50% acetic acid and water. The washes were combined and chromatographed using Sephadex G-50F, eluting with 50% HOAc.

After lyophilization, the partially purified peptide was chromatographed by reverse phase HPLC (Vydac $C_4$ bonded silica, 15 u particle size, 300A pore size, using aqueous acetonitrile gradient containing 0.1% TFA).

EXAMPLE 2

PTH Binding Assay Results

PTH analogues were analysed in a new receptor assay which modified the assay reported in Rosenblatt et al., Endocrin. 107: 545–550 (1980). The binding assay used [Nle$^{8,18}$,$^{125}$I-Tyr$^{34}$]bPTH(1-34)NH$_2$ which was purified by HPLC (Novapak C$_{18}$, 32–35% CH$_3$CN in 0.1% TFA) and was stored as aliquots in 25 mM TrisHCl/1% BSA at −70° C. Bovine renal cortical plasma membranes were incubated with radioligand (25,000 cpm) in a Tris-containing buffer (250 ul) for 30 min. at 21° C. Once equilibrium was reached, bound and free radioligand were separated by centrifugation. High specific binding (85%) to bovine renal cortical membranes was obtained consistently.

TABLE

| Structure | Binding $K_I$(nM) |
| --- | --- |
| [Desamino Tyr$^{34}$]bPTH(7–34)NH$_2$ | 91.0 ± 12.0 |
| [NMePhe$^7$,Tyr$^{34}$]bPTH(7–34)NH$_2$ | 82.0 ± 14.0 |

What is claimed is:

1. A peptide which is
(NMePhe$^7$, Tyr$^{34}$)bPTH(7-34)NH$_2$;
(NMePhe$^7$, Nle$^{8,18}$,Tyr$^{34}$)bPTH(7-34)NH$_2$.

2. A pharmaceutical composition for assaying PTH which comprises an effective amount of a peptide of claim 1 and a pharmaceutically acceptable carrier.